United States Patent
Strobl et al.

(10) Patent No.: US 10,130,410 B2
(45) Date of Patent: Nov. 20, 2018

(54) ELECTROSURGICAL INSTRUMENT INCLUDING A CUTTING MEMBER DECOUPLABLE FROM A CUTTING MEMBER TRIGGER

(71) Applicant: Ethicon Endo-Surgery, LLC, Guaynabo, PR (US)

(72) Inventors: Geoffrey S. Strobl, Williamsburg, OH (US); Cory G. Kimball, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 562 days.

(21) Appl. No.: 14/689,972

(22) Filed: Apr. 17, 2015

(65) Prior Publication Data

US 2016/0302844 A1 Oct. 20, 2016

(51) Int. Cl.
*A61B 18/08* (2006.01)
*A61B 17/3201* (2006.01)
(Continued)

(52) U.S. Cl.
CPC ........ *A61B 18/085* (2013.01); *A61B 17/3201* (2013.01); *A61B 17/3205* (2013.01);
(Continued)

(58) Field of Classification Search
CPC .............. A61B 18/085; A61B 18/1442; A61B 18/1445; A61B 2018/00601;
(Continued)

(56) References Cited

U.S. PATENT DOCUMENTS 2,366,274 A   1/1945   Luth et al.
2,458,152 A   1/1949   Eakins
(Continued)

FOREIGN PATENT DOCUMENTS

CN   2868227 Y    2/2007
CN   102834069 A  12/2012
(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
(Continued)

*Primary Examiner* — Eugene T Wu

(57) ABSTRACT

An electrosurgical instrument. The electrosurgical instrument includes a first arm, a second arm and a coupling system. The first arm includes a first jaw. The second arm is pivotably connected to the first arm and includes a second jaw, a cutting member movable within the first and second jaws, and a cutting member trigger. The coupling system includes a coupling member mechanically coupled to the cutting member trigger. The coupling member is movable between a first position and a second position. In the first position of the coupling member, the cutting member is mechanically uncoupled from the cutting member trigger. In the second position of the coupling member, the cutting member is mechanically coupled to the cutting member trigger.

18 Claims, 7 Drawing Sheets

(51) Int. Cl.
*A61B 17/3205* (2006.01)
*A61B 18/14* (2006.01)
*A61B 18/00* (2006.01)

(52) U.S. Cl.
CPC ............... *A61B 18/1442* (2013.01); *A61B 2018/00601* (2013.01); *A61B 2018/146* (2013.01); *A61B 2018/1457* (2013.01)

(58) Field of Classification Search
CPC .. A61B 2018/00607; A61B 2018/0091; A61B 2018/00916; A61B 2018/00958; A61B 2018/1452; A61B 2018/1455; A61B 17/28; A61B 17/285; A61B 17/29; A61B 17/295; A61B 17/320092; A61B 2017/00353; A61B 2017/00367; A61B 2017/00371; A61B 2017/00384; A61B 2017/1225; A61B 2017/32004; A61B 2017/320072; A61B 90/03; A61B 2090/034; A61B 2090/0801; A61B 2090/08021

See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,314,559 A | 2/1982 | Allen |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |

(56) References Cited

U.S. PATENT DOCUMENTS

| | | |
|---|---|---|
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |
| 5,836,943 A | 11/1998 | Miller, III |
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| 6,409,722 B1 | 6/2002 | Hoey et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,610,060 B2 | 8/2003 | Mulier et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 | 1/2004 | Kornerup |
| 6,682,501 B1 | 1/2004 | Nelson et al. |
| 6,695,840 B2 | 2/2004 | Schulze |
| 6,722,552 B2 | 4/2004 | Fenton, Jr. |
| 6,733,498 B2 | 5/2004 | Paton et al. |
| 6,746,443 B1 | 6/2004 | Morley et al. |
| 6,752,815 B2 | 6/2004 | Beaupre |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |

(56) References Cited

U.S. PATENT DOCUMENTS

| | | |
|---|---|---|
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,283 B2 * | 9/2010 | Shah ............... A61B 17/07207 |
| | | 227/175.1 |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,056,787 B2 | 11/2011 | Boudreaux et al. |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |

(56) References Cited

U.S. PATENT DOCUMENTS

| | | |
|---|---|---|
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,608,044 B2 | 12/2013 | Hueil et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,789,740 B2 * | 7/2014 | Baxter, III ........ A61B 17/07207 227/179.1 |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,017,372 B2 * | 4/2015 | Artale ................ A61B 17/285 606/167 |
| 9,028,494 B2 | 5/2015 | Shelton, IV et al. |
| 9,028,519 B2 | 5/2015 | Yates et al. |
| 9,039,731 B2 | 5/2015 | Joseph |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |

(56) References Cited

U.S. PATENT DOCUMENTS

| | | |
|---|---|---|
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 * | 7/2016 | Artale ............... A61B 17/285 |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,510,906 B2 | 12/2016 | Boudreaux et al. |
| 9,522,029 B2 | 12/2016 | Yates et al. |
| 9,707,005 B2 * | 7/2017 | Strobl ............... A61B 17/3201 |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0131929 A1 | 5/2009 | Shimizu |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2009/0302090 A1 * | 12/2009 | Shah ............... A61B 17/07207 227/180.1 |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |

(56) References Cited

U.S. PATENT DOCUMENTS

| | | |
|---|---|---|
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Homer |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0083827 A1* | 4/2012 | Artale ............... A61B 17/285 606/207 |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0296843 A1 | 11/2013 | Boudreaux et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0180281 A1 | 6/2014 | Rusin |
| 2014/0194874 A1 | 7/2014 | Dietz et al. |
| 2014/0194875 A1 | 7/2014 | Reschke et al. |
| 2014/0194915 A1 | 7/2014 | Johnson et al. |
| 2014/0214019 A1 | 7/2014 | Baxter, III et al. |
| 2014/0221999 A1* | 8/2014 | Cunningham ..... A61B 18/1442 606/52 |
| 2014/0228844 A1 | 8/2014 | Hörlle et al. |
| 2014/0257284 A1 | 9/2014 | Artale |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0336635 A1* | 11/2014 | Hart ................. A61B 17/2804 606/41 |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0317215 A1 | 11/2016 | Worrell et al. |

FOREIGN PATENT DOCUMENTS

| | | |
|---|---|---|
| DE | 4300307 A1 | 7/1994 |
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |

(56) References Cited

FOREIGN PATENT DOCUMENTS

| | | |
|---|---|---|
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2436327 A1 | 4/2012 |
| EP | 2529681 A1 | 12/2012 |
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H 08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40857 A1 | 8/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/008672 A2 | 1/2011 |
| WO | WO 2011/044343 A2 | 4/2011 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

(56) References Cited

OTHER PUBLICATIONS

Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.

\* cited by examiner

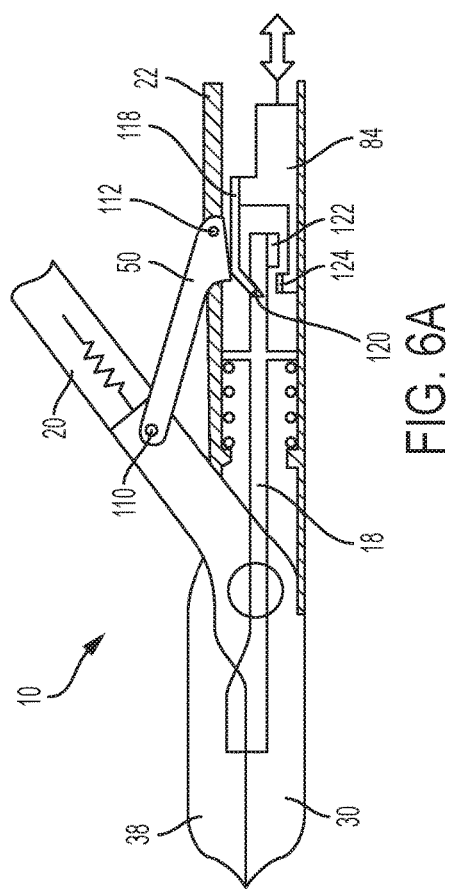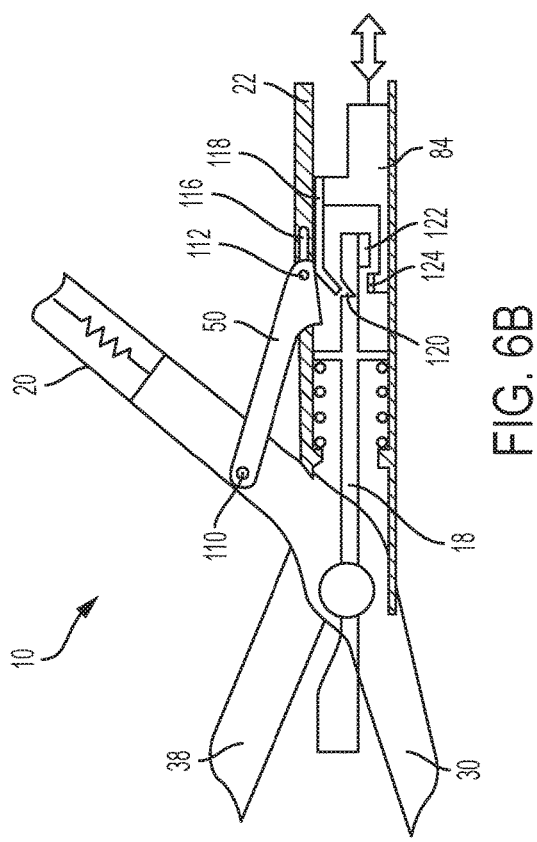

ELECTROSURGICAL INSTRUMENT INCLUDING A CUTTING MEMBER DECOUPLABLE FROM A CUTTING MEMBER TRIGGER

INTRODUCTION

This application discloses, generally and in various embodiments, an electrosurgical instrument including a cutting member, a cutting member trigger and a coupling system configured to couple the cutting member to or decouple the cutting member from the cutting member trigger.

Various surgical instruments include opposing jaws for grasping tissue and a knife for cutting the tissue. Some of these instruments also include one or more electrodes for applying electrosurgical energy to the tissue (e.g., to coagulate or seal the tissue). For such instruments, the instrument can be operated in different modes. For example, such instruments may operate in a grasping only mode, in a grasping and cutting mode, in a grasping and sealing mode and in a grasping, sealing and cutting mode.

For electrosurgical instruments which include opposing jaws for grasping tissue and a knife for cutting the tissue, a knife lockout feature operates to prevent the knife from firing until the opposing jaws are sufficiently closed upon the tissue and/or to prevent the opposing jaws from being opened until the knife has been retracted. Examples of a knife lockout feature are described in U.S. patent application Ser. Nos. 14/579,299, 14/579,599 and 14/579,623, the contents of which are hereby incorporated by reference in their entireties.

Although a knife lockout feature can help prevent accidental cutting by the knife (e.g., by preventing the knife from advancing or retracting even when the trigger is being actuated), such a feature can introduce an unwanted issue. For instances where the trigger is being pulled (or pushed or rotated) prior to the jaws being in an acceptable position for firing of the knife (either distally or proximally), the knife can experience substantial pressure such that when the jaws reach the acceptable position, the knife experiences a very hard release and can quickly shoot to the opposite end of the jaws with an operator of the electrosurgical instrument having little or no control of the speed of the knife.

SUMMARY

In one embodiment, an electrosurgical instrument is provided. The electrosurgical instrument comprises a first arm, a second arm and a coupling system. The first arm comprises a first jaw. The second arm is pivotably connected to the first arm and comprises a second jaw, a cutting member movable within the first and second jaws, and a cutting member trigger. The coupling system comprises a coupling member mechanically coupled to the cutting member trigger. The coupling member is movable between a first position and a second position. In the first position of the coupling member, the cutting member is mechanically uncoupled from the cutting member trigger. In the second position of the coupling member, the cutting member is mechanically coupled to the cutting member trigger.

In another embodiment of the electrosurgical instrument, a proximal end of the first arm is movable from a minimum distance from a proximal end of the second arm to a maximum distance from the proximal end of the second arm. In the first position of the coupling member, the proximal end of the first arm is located at the maximum distance from the proximal end of the second arm. In the second position of the coupling member, the proximal end of the first arm is located at the minimum distance from the proximal end of the second arm.

In another embodiment, the first arm is movable between a first position and a second position and the second arm further comprises a fin member. In the first position of the first arm, the fin member is spaced apart from the coupling member. In the second position of the first arm, the fin member is in contact with the coupling member.

In another embodiment, the second jaw comprises an electrode and the electrosurgical instrument is configured to selectively apply electrosurgical energy to the electrode.

In another embodiment, the first jaw defines a first channel, the second jaw defines a second channel, the first and second channels are axially aligned and the cutting member is movable within the first and second channels.

In another embodiment, the cutting member defines a notch configured to receive the coupling member.

In another embodiment, the electrosurgical instrument further comprises a first protuberance connected to the cutting member and a second protuberance mechanically coupled to the cutting member trigger. At least a portion of the first protuberance is axially aligned with at least a portion of the second protuberance.

In another embodiment, the cutting member defines a receptacle, the coupling member comprises a protuberance and the receptacle is configured to receive the protuberance.

In another embodiment, the coupling system further comprises a movement arm mechanically coupled to the first and second arms. The movement arm is movable between a first position and a second position. In the first position of the movement arm, the movement arm is spaced apart from the coupling member. In the second position of the movement arm, the movement arm is in contact with the coupling member.

In another embodiment, the second arm defines a slot, the coupling system further comprises a pin which mechanically couples the movement arm to the second arm, the pin is slidably movable within the slot and the movement arm is movable along the slot.

In another embodiment, the coupling member is pivotably connected to the cutting member trigger.

In another embodiment, the coupling system further comprises a biasing member in contact with the coupling member. In the first position of the coupling member, the biasing member is in an uncompressed state. In the second position of the coupling member, the biasing member is in a compressed state when the coupling member is in the second position.

In one embodiment, an electrosurgical instrument is provided. The electrosurgical instrument comprises a first arm, a second arm and a coupling system. The first arm comprises a first jaw. The second arm is pivotably connected to the first arm and comprises a second jaw, a cutting member and a cutting member trigger. The second jaw comprises an electrode configured to apply electrosurgical energy to a tissue positioned between the first and second jaws. The cutting member is movable within the first and second jaws and is configured to cut the tissue positioned between the first and second jaws. The coupling system comprises a coupling member mechanically coupled to the cutting member trigger. The coupling member is movable between a first position and a second position. In the first position of the coupling member, movement of the cutting member trigger does not produce distal movement of the cutting member. In the second position of the coupling member, movement of the cutting member trigger produces distal movement of the cutting member.

In another embodiment, the first arm is movable from a first position to a second position. In the first position of the first arm, the first and second jaws are in an open position. In the second position of the first arm, the first and second jaws are in a closed position.

In another embodiment, the coupling system further comprises a movement arm mechanically coupled to the first arm and the second arm.

In another embodiment, the coupling system further comprises a biasing member in contact with the coupling member.

In another embodiment, the movement of the cutting member trigger comprises at least one of the following: a distal movement of the cutting member trigger, a proximal movement of the cutting member trigger and a rotational movement of the cutting member trigger.

In one embodiment, an electrosurgical instrument is provided. The electrosurgical instrument comprises a first arm, a second arm and a coupling system. The first arm comprises a first jaw. The second arm is pivotally connected to the first arm and comprises a second jaw, a cutting member and a cutting member trigger. The second jaw comprises an electrode configured to apply electrosurgical energy to a tissue positioned between the first and second jaws. The cutting member movable within the first and second jaws and is configured to cut the tissue positioned between the first and second jaws. The coupling system comprises a coupling member mechanically coupled to the cutting member trigger. The coupling member is movable between a first position and a second position. In the first position of the coupling member, the cutting member is mechanically uncoupled from the cutting member trigger. In the second position of the coupling member, the cutting member is mechanically coupled to the cutting member trigger.

In another embodiment, the first arm is movable between an open position and a closed position, the coupling member is in the first position when the first arm is in the open position and the coupling member is in the second position when the first arm is in the closed position.

In another embodiment, the first jaw is movable between an open position and a closed position, the coupling member is in the first position when the first jaw is in the open position and the coupling member is in the second position when the first jaw is in the closed position.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows:

FIGS. 6A, 6B and 7 illustrate simplified representations of the electrosurgical instrument of FIG. 1 according to various embodiments.

DESCRIPTION

Figure 1:
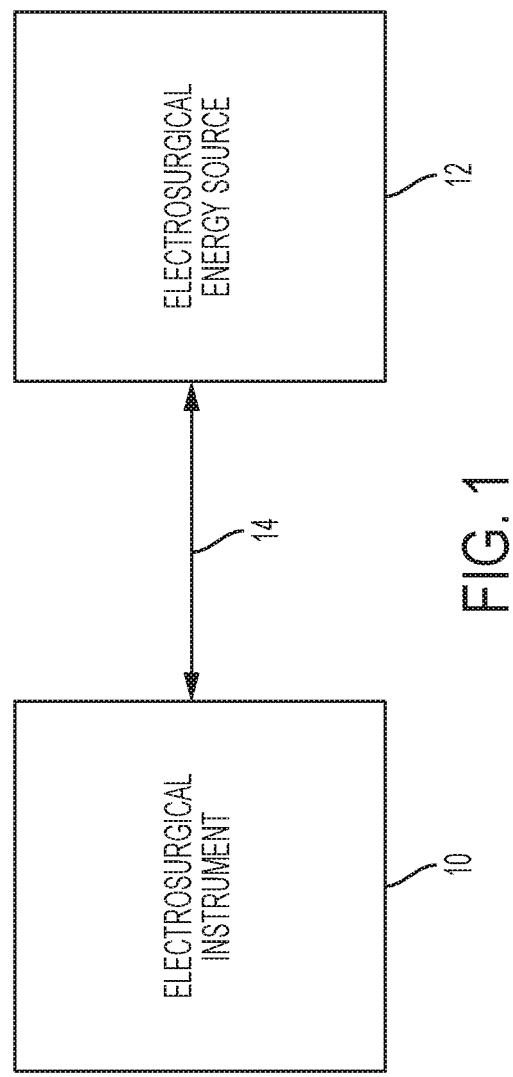
FIG. 1 illustrates a simplified representation of an electrosurgical instrument according to various embodiments.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Before explaining the various embodiments of the electrosurgical instrument including a cutting member decouplable from a cutting member trigger in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the surgical devices disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

Also, in the following description, it is to be understood that terms such as front, back, inside, outside, top, bottom, upper, lower and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

In various embodiments, the present disclosure provides an electrosurgical instrument having a cutting member, a cutting member trigger and a coupling system. The cutting member is decouplable from the cutting member trigger, and the coupling system operates to mechanically couple the cutting member to or decouple the cutting member from the cutting member trigger.

FIG. 1 illustrates a simplified representation of an electrosurgical instrument 10 according to various embodiments. The electrosurgical instrument 10 may be coupled to an electrosurgical energy source 12 via an electrically conductive cable 14. The electrosurgical energy source 12 may be any type of electrosurgical energy source supply suitable for providing electrosurgical energy for therapeutic tissue treatment, tissue cauterization/sealing, as well as sub-therapeutic treatment and measurement. For example, according to various embodiments, the electrosurgical energy source 12 is a voltage supply which can provide electric current to the electrosurgical instrument 10, wherein the magnitude, duration, wave form, and/or frequency, for example, of the electric current can be sufficiently controlled or modulated to provide a desired amount of electrosurgical energy to the electrosurgical instrument 10. Although not shown in FIG. 1 for purposes of simplicity, it will be appreciated that the electrically conductive cable 14 includes at least two electrically conductive wires—one for delivering current from the electrosurgical energy source 12 to the electrosurgical instrument 10 and one for returning current from the electrosurgical instrument 10 to the electrosurgical energy source 12.

As described in more detail hereinbelow, the electrosurgical instrument 10 includes a grasping system, a sealing system, a cutting system and a coupling system. The cutting system includes a cutting member trigger 16 (See FIGS. 2A-2B) and a cutting member 18 (See FIG. 3). The cutting member 18 is normally mechanically decoupled from, but is mechanically couplable to, the cutting member trigger 16. In the mechanically decoupled condition, movement of the cutting member trigger 16 (if possible) does not produce distal or proximal movement of the cutting member 18. The coupling system allows the cutting member 18 to be mechanically coupled to the cutting member trigger 16, and once the cutting member 18 is coupled the cutting member trigger 16, the cutting member trigger 16 can actuate the cutting member 18 (i.e., movement of the cutting member trigger 16 can produce distal or proximal movement of the cutting member 18). According to various embodiments, the electrosurgical instrument 10 also includes a cutting member lockout system, a jaw lock system and/or an electrosurgical energy activation system.

Grasping System

Figure 2:
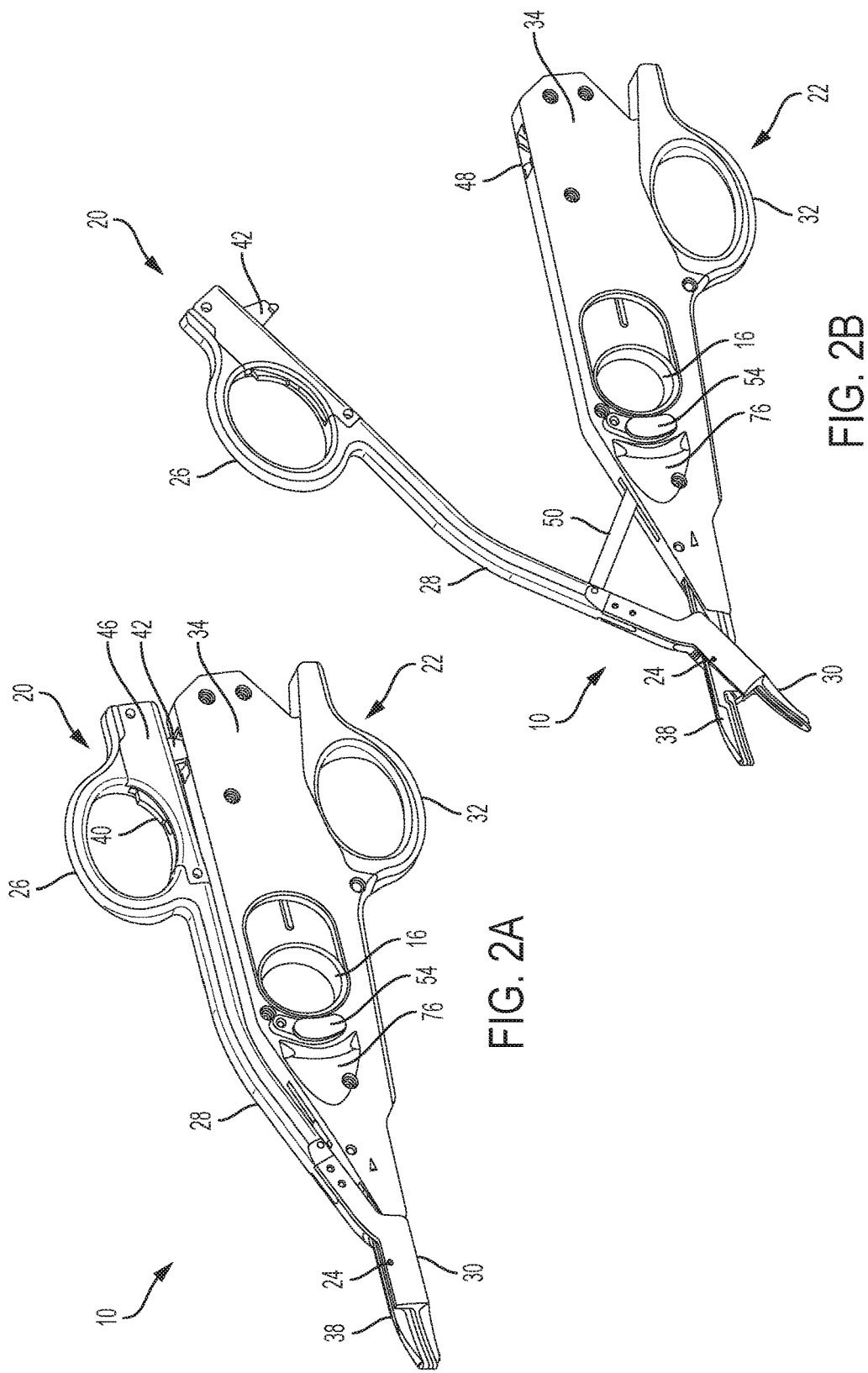
FIG. 2A illustrates a perspective view of various embodiments of the electrosurgical instrument of FIG. 1 in a closed position.
FIG. 2B illustrates a perspective view of various embodiments of the electrosurgical instrument of FIG. 1 in an open position.

FIG. 2A illustrates a perspective view of various embodiments of the electrosurgical instrument 10 in a closed position and FIG. 2B illustrates a perspective view of various embodiments of the electrosurgical instrument 10 in an open position. The electrosurgical instrument 10 includes a first arm 20 and a second arm 22 which are pivotally connected to each other by a pin 24 which is near a distal end of the electrosurgical instrument 10.

According to various embodiments, the first arm 20 includes a finger ring 26, a bend arm 28 and a first jaw 30 (e.g., a lower jaw). The finger ring 26 is near the proximal end of the first arm 16 and is shaped such that a human finger can be inserted therein. The bend arm 28 is between the proximal and distal ends of the first arm 20 and connects the finger ring 26 to the first jaw 30. The first jaw 30 is at the distal end of the first arm 20 and is fixed coupled to the bend arm 28. The finger ring 26, the bend arm 28 and the first jaw 30 are connected in a fixed orientation, such that as the finger ring 26 is moved (e.g., relative to the second arm 22), the bend arm 28 and the first jaw 30 move together with the finger ring 26.

Figure 3:
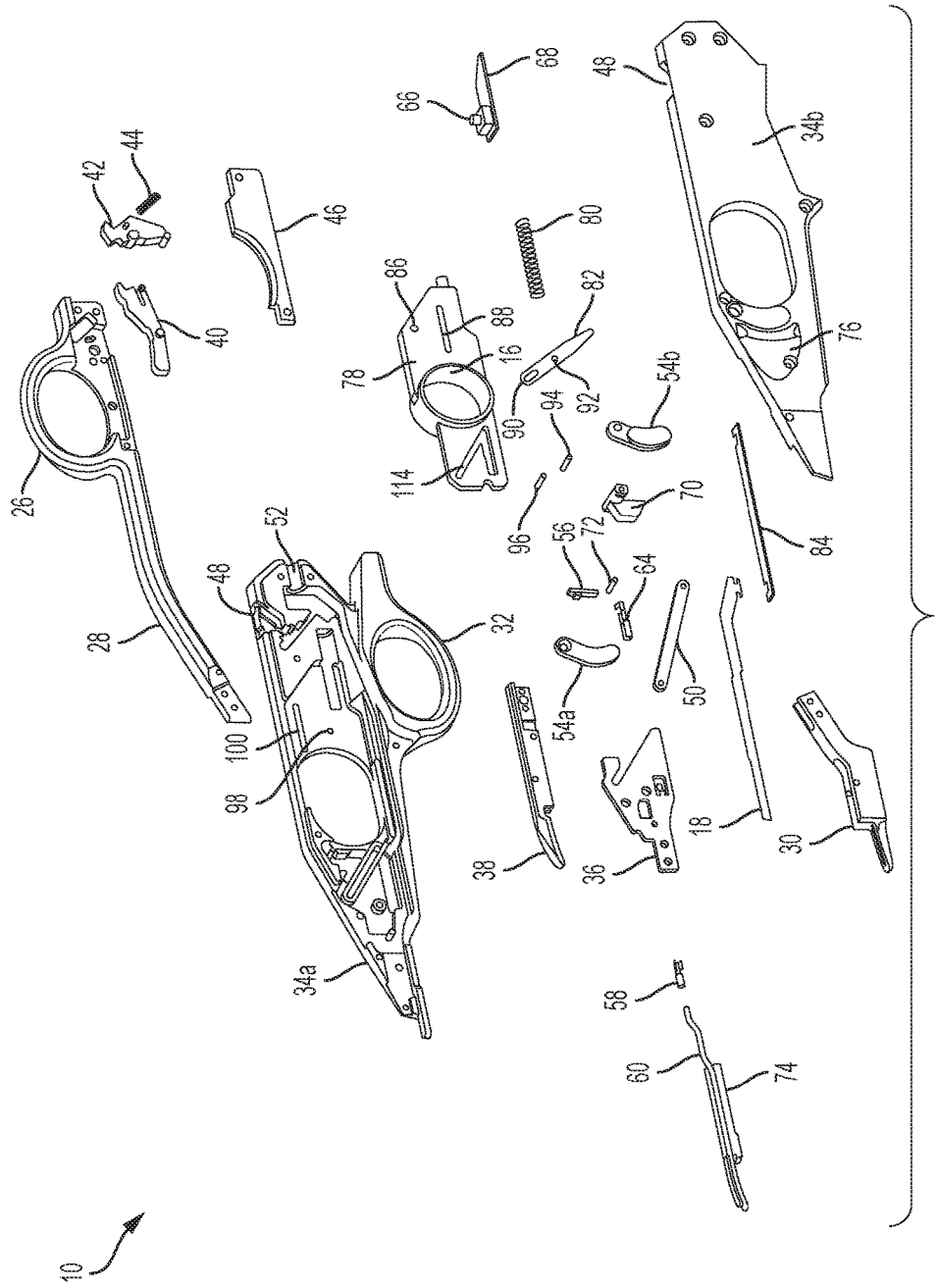
FIG. 3 illustrates an exploded view of the electrosurgical instrument of FIG. 1 according to various embodiments.

According to various embodiments, the second arm 22 includes a finger ring 32, a housing 34, a jaw tail 36 (See FIG. 3) and a second jaw 38 (e.g., an upper jaw). According to various embodiments, the finger ring 32 is formed integral with the housing 34. The finger ring 32 is near the proximal end of the housing 34 and is shaped such that a human finger can be inserted therethrough. The jaw tail 36 is positioned within the distal end of the housing 34 and is fixedly coupled to the housing 34 and the proximal end of the second jaw 36. The finger ring 32, the housing 34, the jaw tail 36 and the second jaw 38 are connected in a fixed orientation, such that as the finger ring 32 is moved, the housing 34, the jaw tail 36 and the second jaw 38 move together with the finger ring 32. According to various embodiments, the housing 34 includes a first portion 34a (e.g., a left portion) and a second portion 34b, and the finger ring 32 may be formed integral with the first portion 34a of the housing 34 as shown in FIG. 3.

The first and second jaws 30, 38 are movable relative to one another between a first position (e.g., a closed position as shown in FIG. 2A) and a second position (e.g., an open position as shown in FIG. 2B). The movement of the first and second jaws 30, 38 is similar to the movement experienced by the pivotable blades of a pair of scissors. In operation, starting from the open position, where the distal ends of the first and second jaws 30, 38 are spaced a maximum distance apart from each other, a tissue (not shown) may be positioned between the first and second jaws 30, 38. As the first and second jaws 30, 38 are moved toward one another (e.g., by moving the finger ring 26 toward the finger ring 32), the tissue positioned between the first and second jaws 30, 38 is grasped and compressed. It will be appreciated that the finger ring 26, the bend arm 28, the first jaw 30, the finger ring 32, the housing 34, the jaw tail 36 and the second jaw 38 may be considered components of the grasping system of the electrosurgical instrument 10. Additional details of the grasping system can be found, for example, in U.S. patent application Ser. Nos. 14/579,299, 14/579,599 and 14/579,623, the contents of which are hereby incorporated by reference in their entireties. From the closed position, where the distal ends of the first and second jaw members 30, 38 are spaced a minimum distance apart from each other, the first and second jaws 30, 38 may be moved toward the open position by moving the finger ring 26 away from the finger ring 32.

The electrosurgical instrument 10 is configured such that it can be easily operated by a right-handed person or a left-handed person in the orientation shown in FIGS. 2A-2B or upside down from the orientation shown in FIGS. 2A-2B. In the orientation shown in FIGS. 2A-2B, the operator can place their thumb in the finger ring 26 and one or more of their other fingers in the finger ring 32, then manipulate their fingers to cause the first and second jaws 30, 38 to open and close. In an orientation which is upside down from the orientation shown in FIGS. 2A-2B, the operator can place their thumb in the finger ring 32 and one or more of their other fingers in the finger ring 26, then manipulate their fingers to cause the first and second jaws 30, 38 to open and close. As such, the terms upper, lower, left and right are used for convenience only, and not as a limitation. Also, although the finger rings 26, 32 are shown as being substantially similar in size and configuration, it will be appreciated that according to other embodiments the finger rings 26, 32 may be of different sizes and/or configurations.

According to various embodiments, the first arm 20 also includes a lock button 40, a switch arm 42, a biasing member 44 (See FIG. 3) and a cover member 46. For such embodiments, the second arm 22 also includes a switch arm slot 48. As described in more detail hereinbelow, the lock button 40, the switch arm 42, the biasing member 44 (e.g., a spring) and the switch arm slot 48 may be considered components of the jaw lock system of the electrosurgical instrument 10 and/or the electrosurgical energy activation system of the electrosurgical instrument 10. As shown in FIG. 2B, according to various embodiments, the electrosurgical instrument 10 may also include a movement arm 50 mechanically coupled to the first and second arms 20, 22. As described in more detail hereinbelow, the movement arm 50 may be considered a component of the cutting member lockout system of the electrosurgical instrument 10.

Sealing System

FIG. 3 illustrates an exploded view of the electrosurgical instrument 10 according to various embodiments. According to various embodiments, the second arm 22 also includes a port 52, an energy button 54, an energy button circuit 56, an electrode connector 58, an electrode 60, an electrically conductive jaw stop 62 (See FIG. 4B) and a return connector 64. For such embodiments, the second arm 22 may further include a compression circuit button 66 and a compression circuit 68. The port 52 is configured to receive an end of the electrically conductive cable 14 to electrically couple the electrosurgical energy source 12 to the electrosurgical instrument 10. Although not shown in FIG. 3 for purposes of simplicity, it will be appreciated that according to various embodiments, the second arm 22 includes wiring for electrically connecting the energy button circuit 56 to the port 52, wiring for electrically connecting the electrode 60 (or the electrode connector 58) to the port 52, wiring and/or electrically conductive members for electrically connecting the first jaw 30, the second jaw 38 and/or the electrically conductive jaw stop 62 to the return connector 64, wiring for electrically connecting the return connector 64 to the port 52 and wiring for electrically connecting the compression circuit 68 to the port 52. According to various embodiments, the energy button circuit 56 comprises a portion of a first electrical circuit (e.g., a switch circuit) and the electrode 60 comprises a portion of a second electrical circuit (e.g., an electrosurgical energy circuit). For such embodiments, the two circuits can share a common neutral connector to the port 52 (and from the port 52 to the electrosurgical energy source 12).

The electrode 60 runs along the length of the second jaw 38 and extends into the housing 34. The proximal end of the electrode 60 positioned in the housing 34 is electrically connected to the electrode connector 58. The electrode connector 58 is electrically connected to the port 52 via wiring (not shown for purposes of simplicity). In some embodiments, the selective application of the electrosurgical energy to the electrode 60 can be controlled by the energy button 54. The energy button 54 is movable from a first position (e.g., a "normally open" position) to a second position (e.g., a "closed" position). As shown in FIG. 3, the energy button 54 can include a first body portion 54a (e.g., the left portion), a second body portion 54b (e.g., the right portion), a rocker 70 that is configured to allow the energy button 54 to pivot and a pin 72 that mechanically couples the rocker 70 to the first and second body portions 54a, 54b of the energy button 54. According to various embodiments, after the energy button 54 is activated, the energy button circuit 56 signals the electrosurgical energy source 12 to deliver electrosurgical energy (e.g., bipolar radio-frequency energy) to the electrode 60. As described hereinabove, the electrosurgical energy source 12 can deliver the electrosurgical energy to the port 52 via the conductive cable 14, from the port 52 to the electrode connector 58 via wiring and from the electrode connector 58 to the electrode 60.

According to various embodiments, if the energy button 54 is in the first position, the energy button circuit 56 does not signal the electrosurgical energy source 12 to deliver electrosurgical energy to the electrode 60 and thus no electrosurgical energy is applied by the electrode 60 to tissue positioned between the first and second jaws 30, 38. For such embodiments, if the energy button 54 is moved to the second position, the energy button circuit 56 signals the electrosurgical energy source 12 to deliver electrosurgical energy to the electrode 60 and the delivered electrosurgical energy is applied by the electrode 60 to tissue positioned between the first and second jaws 30, 38 to seal or coagulate the tissue.

Figure 4:
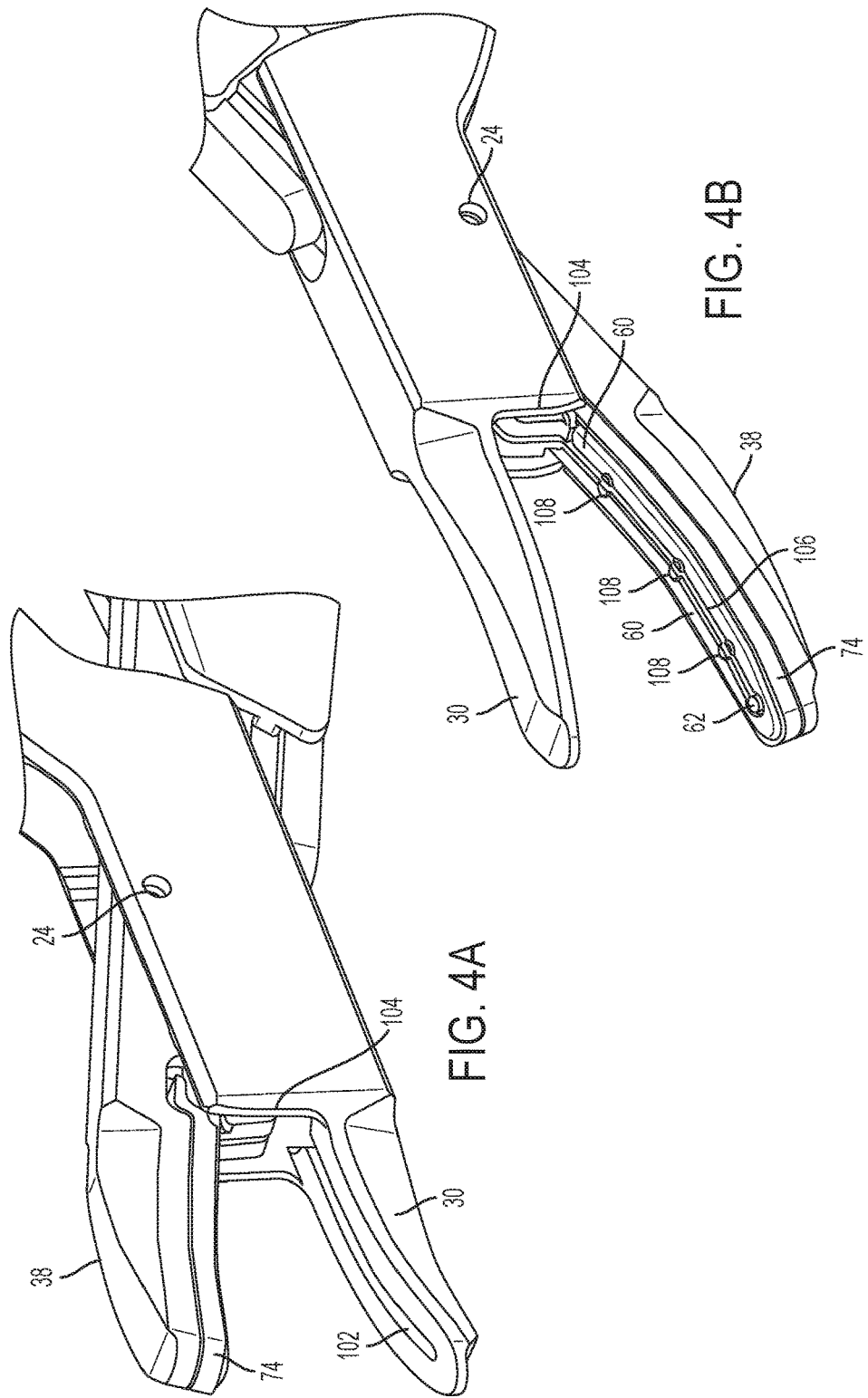
FIGS. 4A and 4B illustrate various embodiments of first and second jaws of the electrosurgical instrument of FIG. 1 when the first and second jaws are in an open position.

The current return path from the electrode 60 to the electrosurgical energy source 12 may include the tissue positioned between the first and second jaws 30, 38, the first jaw 30, and the second jaw 38 via the electrically conductive jaw stop 62. Each of the first and second jaws 30, 38 can comprise portions of the current return path and can be electrically connected to the port 52 in any reasonable manner. For example, in various embodiments, the first and second jaws 30, 38 are electrically connected to the port 52 via the return connector 64 and wiring from the return connector 64 to the port 52. In other embodiments, the first and second jaws 30, 38 are soldered/welded directly to wiring which is electrically connected to the port 52. As shown in FIG. 4B, the electrically conductive jaw stop 62 is positioned at the distal end of the second jaw 38, extends above a tissue-facing surface of the second jaw 38 and operates to set a minimum gap between the first and second jaws 30, 38. It will be appreciated that the port 52, the energy button 54, the energy button circuit 56, the electrode connector 58, the electrode 60, the electrically conductive jaw stop 62 and the return connector 64 may be considered components of the sealing system of the electrosurgical instrument 10.

According to various embodiments, the second arm 22 includes the compression circuit button 66 and the compression circuit 68. The compression circuit button 66 is movable from a first position (e.g., a "normally open" position) and a second position (e.g., a "closed" position). The compression circuit 68 may be wired and configured to signal the electrosurgical energy source 12 when the compression circuit button 66 is in the closed position. In some embodiments, only the energy button 54 needs to be in the closed position in order for electrosurgical energy to be delivered to the electrode 60. In other embodiments, the energy button 54 and the compression circuit button 66 both need to be in their respective closed positions in order for electrosurgical energy to be delivered to the electrode 60. In yet other embodiments, only the compression circuit button 66 needs to be in the closed position in order for electrosurgical energy to be delivered to the electrode 60. Details of how the compression circuit button 66 can be placed into the closed position are described hereinbelow. It will be appreciated that according to various embodiments, the compression circuit button 66 and the compression circuit 68 may also be considered components of the sealing system of the electrosurgical instrument 10.

In general, when tissue is positioned between the first and second jaws 30, 38 and the compression circuit button 66 is in the closed position, the first and second jaws 30, 38 apply sufficient compression to the tissue to enable a good seal of the tissue when the electrode 60 applies electrosurgical energy to the tissue. According to various embodiments, responsive to the signal received from the compression circuit 68, the electrosurgical energy source 12 may generate an end tone or tissue seal completion signal when the tissue is sufficiently sealed and ready to be cut by the cutting member 18. In some embodiments, when the compression circuit button 66 is in the open position, electrosurgical energy is not delivered to the electrode 60 and/or the end tone or tissue seal completion signal is not generated.

According to various embodiments, the electrosurgical instrument 10 further includes an insulator 74 which is mechanically coupled to and surrounds the electrode 60. According to various embodiments, the electrode 60 and the insulator 74 form portions of the second jaw 38. As shown in FIG. 3, the second arm 22 may further include a bump 76 connected to the housing 34. The bump 76 may be formed integral with the housing 34 and operates to prevent accidental activation of the energy button 54. Although the bump 76 is shown as being connected to the second portion 34b of the housing 34, it will be appreciated that a similar bump (hidden from view in FIG. 3) may also be connected to the first portion 34a of the housing 34. Additional details of the sealing system can be found, for example, in U.S. patent application Ser. Nos. 14/579,299, 14/579,599 and 14/579,623, the contents of which are hereby incorporated by reference in their entireties.

Cutting System

As described hereinabove, the cutting member 18 is normally mechanically uncoupled from, but is mechanically couplable to, the cutting member trigger 16 which actuates the cutting member 18. Although the cutting member trigger 16 is shown as a pull ring in FIG. 3, it will be appreciated that the cutting member trigger 16 may be configured in a number of different ways. As described in more detail hereinbelow, once the cutting member 18 is mechanically coupled to the cutting member trigger 16, the distal end of the cutting member 18 can be advanced from its unfired position in the housing 34 toward the distal end of the electrosurgical instrument 10 to cut tissue positioned between the first and second jaws 30, 38. The cutting member 18 can also be retracted proximally back to its unfired position in the housing 34. The cutting member trigger 16 provides an operator of the electrosurgical instrument 10 control of the cutting member 18.

For the embodiments shown in FIG. 3, once the cutting member 18 is mechanically coupled to the cutting member trigger 16, movement of the cutting member trigger 16 toward the proximal end of the electrosurgical instrument 10 causes the advancement of the cutting member 18 toward the distal end of the electrosurgical instrument 10. According to various embodiments, as shown in FIG. 3, the second arm 22 also includes a plate member 78, a biasing member 80, a push arm 82 and a slide 84. According to various embodiments, the plate member 78 is formed integral with the cutting member trigger 16. Stated differently, in some embodiments, the cutting member trigger 16 includes a pull ring and the plate member 78. The plate member 78 defines an opening 86 and a slot 88, and is mounted within the housing 34 such that the plate member 78 is able to slide along the proximal-distal axis of the electrosurgical instrument 10. The proximal end of the plate member 78 rests against the biasing member 80 (e.g., a spring). When the biasing member 80 is in a relaxed or minimally compressed state as shown in FIG. 3, the plate member 78 is in a distal or neutral position and the distal end of the cutting member 18 is in an unfired or retracted position within the housing 34 (i.e., it is not exposed between the first and second jaws 30, 38). The push arm 82 defines a slot 90 and an opening 92, and is mechanically coupled to the plate member 78 by a pin 94 and a pin 96. The pin 94 passes through the opening 92 of the push arm 82 and the slot 88 of the plate member 78, and is mounted within matching openings 98 defined by the first and second portions 34a, 34b of the housing 34 (the opening 94 defined by the second portion 34b of the housing 34 is hidden from view in FIG. 3). The pin 96 passes through the slot 90 of the push arm 82 and the opening 86 of the plate member 78, and is mounted within matching slots 100 defined by the first and second portions 34a, 34b of the housing 34 (the slot 100 defined by the second portion 34b of the housing 34 is hidden from view in FIG. 3). The bottom end of the push arm 82 is mechanically coupled to the slide 84 near the proximal end of the slide 84, and the slide 84 is mechanically coupled to the proximal end of the cutting member 18 near the distal end of the slide 84.

When an operator applies a force to the cutting member trigger 16 to move the cutting member trigger 16 in a proximal direction, the pin 94 mounted within the matched openings 98 doesn't move proximally or distally, the pin 96 mounted within the matched slots 100 moves proximally within the slots 100, the slot 88 of the plate member 78 slides over the pin 94 allowing the plate member 78 to move proximally, the biasing member 80 becomes compressed and the push arm 82 pivots relative to the plate member 78. The pivoting of the push arm 82 causes the slot 90 of the push arm 82 to slide proximally over the pin 96, the top of the push arm 82 to move proximally and the bottom of the push arm 82 to move distally. The distal movement of the bottom of the push arm 82 causes the slide 84 to move distally and the distal movement of the slide 84 causes the cutting member 18 to advance distally from its unfired position within the housing 34 toward the distal end of the electrosurgical instrument 10. When the operator removes the force from the cutting member trigger 16, the biasing member 80 decompresses and moves the plate member 78 distally which causes the push arm 82 to pivot relative to the plate member 78. The pivoting of the push arm 82 causes the slot 90 of the push arm 82 to slide distally over the pin 96, the top of the push arm 82 to move distally and the bottom of the push arm 82 to move proximally. The proximal movement of the bottom of the push arm 82 causes the slide 84 to move distally and the distal movement of the slide 84 causes the cutting member 18 to retract proximally toward the proximal end of the electrosurgical instrument 10 back to its unfired position within the housing 34. In various embodiments, the plate member 78 may be replaced with a ring plate, without limitation.

Although the distal advancement of the cutting member 18 is described as being actuated by pulling the cutting member trigger 16 in the proximal direction, it will be appreciated that according to other embodiments, the distal advancement of the cutting member 18 can be actuated by pushing the cutting member trigger 16 in a distal direction, rotating the cutting member trigger 16, etc. Similarly, although the proximal retraction of the cutting member 18 is described as being actuated by pushing the cutting member trigger 16 in the distal direction, it will be appreciated that according to other embodiments, the proximal retraction of the cutting member 18 can be actuated by pulling the cutting member trigger 16 in a proximal direction, rotating the cutting member trigger 16, etc.

FIGS. 4A and 4B illustrate various embodiments of the first and second jaws 30, 38 when the first and second jaws 30, 38 are in an open position. In the open position, tissue may be positioned between the first and second jaws 30, 38. In FIG. 4A, the electrosurgical instrument 10 is oriented so that the first jaw 30 is oriented below the second jaw 38 and the tissue-facing surface of the first jaw 30 is visible. The first jaw 30 defines a slot 102 configured so that the cutting member 18 can translate therein. The first jaw 30 also includes a tissue stop 104 configured to limit or block tissue positioned between the first and second jaws 30, 38 from advancing any further towards the proximal end of the first and second jaws 30, 38. In some embodiments, the tissue-facing surface of the first jaw 30 is substantially smooth. In one embodiment, the slot 102 may be configured as a channel defining a base and laterally opposed sidewalls extending outwardly from the base.

In FIG. 4B, the electrosurgical instrument 10 is oriented so that the second jaw 38 is oriented below the first jaw 30 and the tissue-facing surface of the second jaw 38 is visible. The second jaw 38 includes the electrode 60 and the insulator 74 which partially surrounds the electrode 60. According to various embodiments, the electrode 60 is a U-shaped electrode which extends from the interior of the housing 34 along one side of the second jaw 38 to the distal end of the second jaw 38 and returns along the other side of the second jaw 38, ending behind the tissue stop 104. The body of the electrode 60 thus defines a slot 106 within which the cutting member 16 can translate. In one embodiment, the slot 106 may be configured as a channel defining a base and laterally opposed sidewalls extending outwardly from the base. The slot 102, or channel, defined by the first jaw 30 is axially aligned with the slot 106, or channel, defined by the second jaw 38. As shown in FIG. 4B, the second jaw 38 may include one or more non-conductive teeth 108 and the electrically conductive jaw stop 62. The non-conductive teeth 108 are positioned along the tissue-facing surface of the electrode 60 and are configured to assist in gripping tissue placed between the first and second jaws 30, 38. The electrically conductive jaw stop 62 is positioned at the distal end of the second jaw 38, extends above the tissue-facing surface of the second jaw 38 and operates to set a minimum gap between the first and second jaws 30, 38. It will be appreciated that the cutting member trigger 16, the cutting member 18, the first and second jaws 30, 38, the plate member 78, the biasing member 80, the push arm 82, and the slide 84 may be considered components of the cutting system of the electrosurgical instrument 10.

Additional details of the cutting system can be found, for example, in U.S. patent application Ser. Nos. 14/579,299, 14/579,599 and 14/579,623, the contents of which are hereby incorporated by reference in their entireties. Furthermore, it will be appreciated that the sealing system and the cutting system can be used separately or together. That is, the operator of the electrosurgical instrument 10 can choose to activate the sealing system without also activating the cutting system. Similarly, the operator can choose to activate the cutting system without also activating the sealing system. The operator can also choose to seal and cut, typically in that order, by activating the sealing system and subsequently activating the cutting system.

Cutting Member Lockout System

Safe and effective operation of the cutting member 18 may raise at least two concerns that may be addressed by the cutting member lockout system. First, it may be desirable to prevent the cutting member 18 from firing until the first and second jaws 30, 38 are sufficiently closed to cut the tissue held by the first and second jaws 30, 38. Second, it may be desirable to prevent the first and second jaws 30, 38 from opening until the cutting member 18 has been retracted. The first safety concern seeks to prevent the first and second jaws 30, 38 from being wider apart than the cutting member 18 is tall, so that the cutting member 18 will always cut through all layers of the tissue held by the first and second jaws 30, 38. The second safety concern seeks to prevent the cutting member 18 from being exposed and inadvertently cutting tissue that was not meant to be cut.

Figure 5:
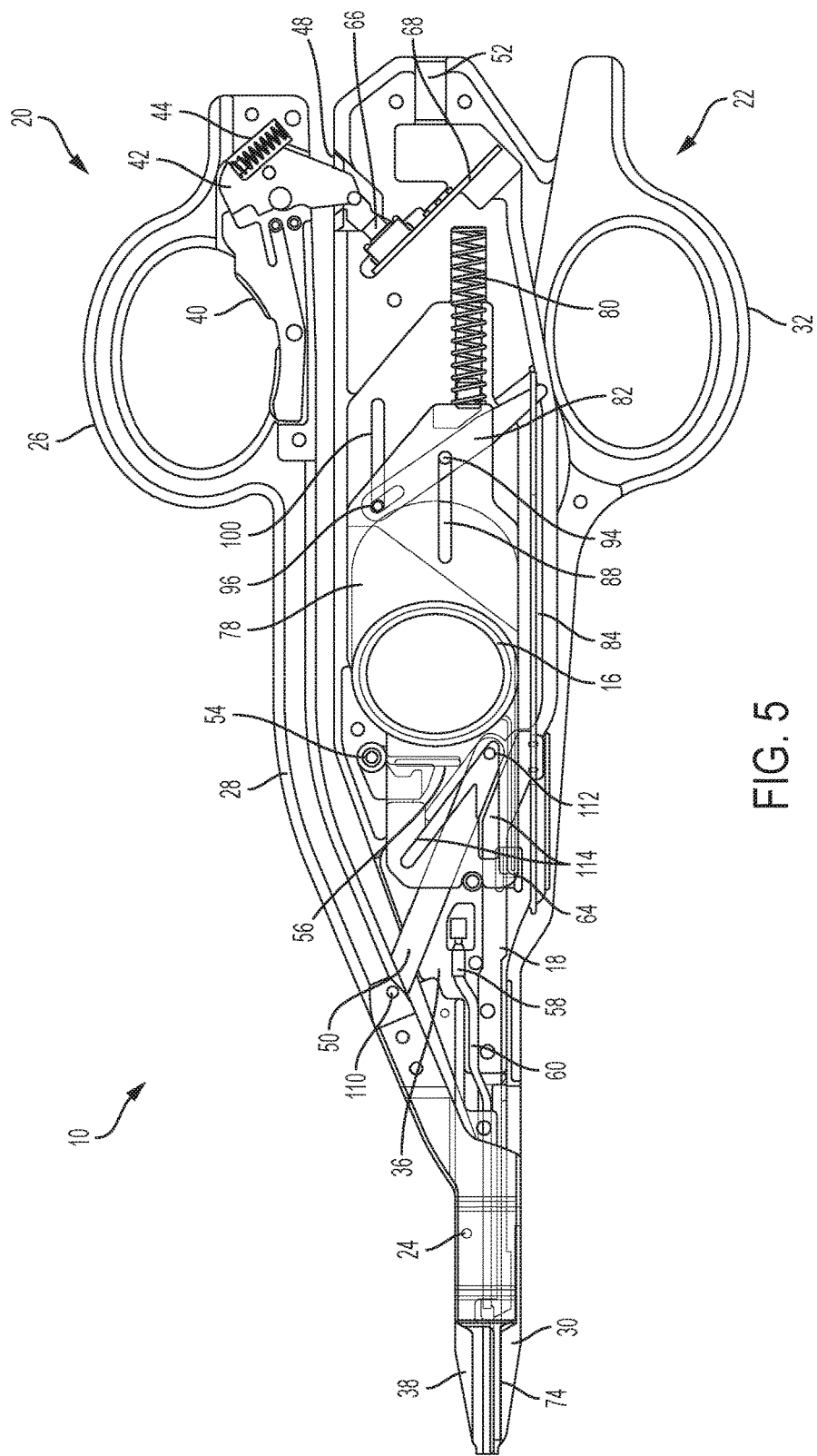
FIG. 5 illustrates a sideways transparent view of the electrosurgical instrument of FIG. 1 according to various embodiments.

FIG. 5 illustrates a sideways transparent view of the electrosurgical instrument 10 according to various embodiments. As shown in FIG. 5, a distal end of the movement arm 50 is pivotably connected to the first arm 20 by a pin 110, and a proximal end of the movement arm 50 is mechanically coupled to the plate member 78 by a pin 112 which passes through the proximal end of the movement arm 50 and through a slot 114 defined by the plate member 78. The movement arm 50 provides a link between the first arm 20 and the cutting member trigger 16 (which may include the plate member 78). As the first arm 20 is moved away from the second arm 22, the pin 112 rides upward in the slot 114. When the first and second jaws 30, 38 reach the fully open position, the pin 112 is at the top of the slot 114. The slot 114 is shaped such that the pin 112 prevents the plate member 78 from moving until the first and second jaws 30, 38 are partially or entirely closed.

In some embodiments, the slot 114 comprises an angled "L" shape such that the upper or upright arm portion of the slot 114 is at an angle to the direction of travel of the plate member 78 and the lower or horizontal portion of the slot 114 is parallel to the direction of travel of the plate member 78. In such embodiments, the angle of the upright arm portion of the slot 114 and the location of the pin 112 within the upright arm portion of the slot 114 prevents the plate member 78 from moving forwards or backwards. The pin 112 must travel to the horizontal portion of the slot 114 in order for the plate member 78 to be able to move. The horizontal portion of the slot 114 is positioned parallel to the direction of travel of the plate member 78. The position of the pin 112 within the horizontal portion of the slot 114 thus operates to prevent the first and second jaws 30 38 from being opened. The plate member 78 must be returned to the neutral position such that the pin 112 can access the upright arm portion of the slot 114 before the first and second jaws 30, 38 can be opened.

It will be appreciated that the movement arm 50 and the plate member 78 may be considered components of the cutting member lockout system of the electrosurgical instrument 10. Additional details of the cutout member locking system can be found, for example, in U.S. patent application Ser. Nos. 14/579,299, 14/579,599 and 14/579,623, the contents of which are hereby incorporated by reference in their entireties.

Coupling System

Figure 7:
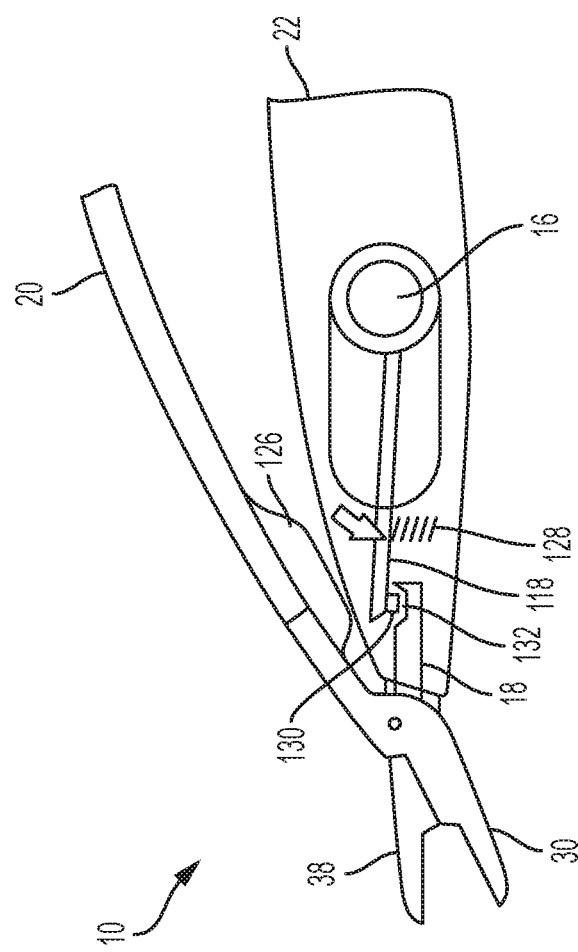

FIGS. 6A, 6B and 7 illustrate simplified representations of the electrosurgical instrument 10 of FIG. 1 according to various embodiments. For purposes of simplicity, certain components described hereinabove of the electrosurgical instrument 10 are not shown in FIGS. 6A, 6B and 7. As shown in FIGS. 6A, 6B and 7, the electrosurgical instrument 10 further includes a coupling member 118. FIG. 6A shows the coupling member 118 in contact with the cutting member 18 when the first and second jaws 30, 38 are in a closed position, and FIG. 6B shows the coupling member 118 uncoupled from the cutting member 18 when the first and second jaws 30, 38 are in an open position. The coupling member 118 may be configured in any manner suitable for mechanically coupling the cutting member 18 to the cutting member trigger 16 The cutting member trigger 16 and the cutting member 18 may be configured in any manner suitable for being mechanically coupled to one another via the coupling member 118. According to various embodiments, the coupling member 118 is a flexible member (e.g., a leaf spring) which is fixedly connected to the slide 84 (the slide 84 is shown in FIGS. 3 and 5) and has a bent or hooked distal end (e.g., See FIGS. 6A and 6B). According to other embodiments, the coupling member 118 is a flexible member which defines a downward extending protuberance and is fixedly connected to the slide 84 at its distal end. According to yet other embodiments, the coupling member 118 is a rigid member which is pivotably connected to the cutting member trigger 16 and includes a downward extending protuberance at its distal end (e.g., See FIG. 7). According to yet other embodiments, the coupling member 118 is a cam member.

For the embodiments shown in FIGS. 6A and 6B, the coupling member 118 is a leaf spring which has a bent or hooked distal end, the coupling member 118 is fixedly connected to the slide 84, the cutting member 18 defines a notch 120 near its proximal end, the notch 120 is configured to receive the bent or hooked distal end of the coupling member 118, a protuberance 122 is connected to the bottom of the cutting member 18 near its proximal end and a protuberance 124 is connected to the slide 84 near its distal end. The protuberances 122 and 124 are aligned such that movement of the slide 84 in the proximal direction causes the engagement of the protuberances 122, 124 and movement of the cutting member 18 in the proximal direction (retraction). According to various embodiments, the protuberance 122 is formed integral with the cutting member 18 and/or the protuberance 124 is formed integral with the slide 84. The upper end of the movement arm 50 is still mechanically coupled to the first arm 20 by the pin 110, but the pin 112 which mechanically couples the lower end of the movement arm 50 to the second arm 22 is movably positioned in a slot 116 which is defined by the second arm 22 (instead of in the slot 114 of the plate member 78). As described hereinabove, the slide 84 is mechanically coupled to the push arm 82, which is mechanically coupled to the plate member 78, which can be formed integral with the cutting member trigger 16. Thus, when the coupling member 118 is seated in the notch 120 of the cutting member 18 as shown in FIG. 6A, the cutting member 18 is mechanically coupled to the cutting member trigger 16.

When the first and second jaws 30, 38 are in the open position, the distal end of the coupling member 118 is positioned above the notch 120 of the cutting member 16 and the cutting member 18 is mechanically decoupled from the cutting member trigger 16. In this mechanically decoupled condition, movement of the cutting member trigger 16 (if possible) does not cause any distal advancement of the cutting member 18. As the first and second jaws 30, 38 are moved toward the closed position, the pin 112 slides proximally in the slot 116 and the proximal end of the movement arm 50 moves proximally. Due to the configuration of the proximal end of movement arm 50, as the movement arm 50 moves proximally, the movement arm 50 pushes down on the coupling member 118, causing the distal end of the coupling member 118 to move toward the notch 120. When the first and second jaws 30, 38 are in the closed position, due to the downward force applied by the proximal end of the movement arm 50 on the coupling member 118, the coupling member 118 is positioned in the notch 120 and the cutting member 18 is mechanically coupled to the cutting member trigger 16. In this mechanically coupled condition, when the cutting member trigger 16 is pulled proximally, the slide 84 and the coupling member 118 move distally thereby causing the cutting member 18 to advance distally.

Regardless of whether or not the cutting member 18 is coupled to or decoupled from the cutting member trigger 16, when the cutting member trigger 16 is pushed distally, the slide 82 and the protuberance 124 move proximally. The proximal movement of the protuberance 124 causes it to engage with the protuberance 122 and move the protuberance 122 proximally thereby causing the retraction of the cutting member 18. Thus, it will be appreciated that the cutting member 18 can always be retracted from an extended state regardless of the position of the first and second jaws 30, 38.

Although the distal advancement of the cutting member 18 is described with respect to FIGS. 6A, 6B and 7 as being actuated by pulling the cutting member trigger 16 in the proximal direction, it will be appreciated that according to other embodiments, the distal advancement of the cutting member 18 can be actuated by pushing the cutting member trigger 16 in a distal direction, rotating the cutting member trigger 16, etc. Similarly, although the proximal retraction of the cutting member 18 is described as being actuated by pushing the cutting member trigger 16 in the distal direction, it will be appreciated that according to other embodiments, the proximal retraction of the cutting member 18 can be actuated by pulling the cutting member trigger 16 in a proximal direction, rotating the cutting member trigger 16, etc.

For the embodiments shown in FIG. 7, the first arm 20 further includes a fin member 126, and the second arm 22 further includes a biasing member 128 and the coupling member 118. The fin member 126 extends in a downward direction from the bottom side of the first arm 20. According to various embodiments, the fin member 126 is formed integral with the first arm 20. The biasing member 128 operates to push up on the coupling member 118.

For these embodiments, the coupling member 118 is a solid member which includes a downward extending protuberance 130 near its distal end, the coupling member 118 is pivotably connected to the cutting member trigger 16 (or to a component which is formed integral with the cutting member trigger 16), the cutting member 18 defines a receptacle 132 near its proximal end and the receptacle 132 is configured to receive the protuberance 130. According to various embodiments, the protuberance 130 is formed integral with the coupling member 118. According to other embodiments, the protuberance 130 is a separate component which is connected to the coupling member 118. The movement arm 50 may still be mechanically coupled to the first arm 20 by the pin 110 and to the plate member 78 by the pin 112, or the movement arm 50 and the pins 110, 112 can be eliminated.

When the first and second jaws 30, 38 are in the open position, the proximal ends of the first and second arms 20, 22 are spaced apart from one another, the fin member 126 is positioned above and is not in contact with the coupling member 118, the biasing member 128 is in a relaxed or minimally compressed state and is in contact with the coupling member 118, and the cutting member 18 is mechanically decoupled from the cutting member trigger 16. In this mechanically decoupled condition, movement of the cutting member trigger 16 (if possible) does not cause any distal advancement of the cutting member 16. As the first and second jaws 30, 38 are moved toward the closed position (by moving the first arm 20 toward the second arm 22), the fin member 126 moves toward the top of the coupling member 118, eventually making contact with and pushing down on the coupling member 118, causing the biasing member 128 to compress, the coupling member 118 to pivot in a downward direction and the protuberance 130 to start being received by the receptacle 132. When the first and second jaws 30, 38 are in the closed position, due to the downward force applied by the fin member 126, the biasing member 128 is in a compressed condition, the protuberance 130 is positioned in the receptacle 132 and the cutting member 18 is mechanically coupled to the cutting member trigger 16. In this mechanically coupled condition, when the cutting member trigger 16 is pushed distally, the coupling member 118 moves distally and the protuberance 130 moves distally, causing the cutting member 18 to advance distally. When the cutting member trigger 16 is pulled proximally, the coupling member 118 moves proximally and the protuberance 130 moves proximally, causing the cutting member 18 to retract.

Although the distal advancement of the cutting member 18 is described with respect to FIG. 7 as being actuated by a pushing of the cutting member trigger 16 in the distal direction, it will be appreciated that according to other embodiments, the distal advancement of the cutting member 18 can be actuated by a pulling of the cutting member trigger 16 in a proximal direction, a rotation of the cutting member trigger 16, etc. Similarly, although the proximal retraction of the cutting member 18 is described as being actuated by a pulling of the cutting member trigger 16 in the proximal direction, it will be appreciated that according to other embodiments, the proximal retraction of the cutting member 18 can be actuated by a pushing of the cutting member trigger 16 in a distal direction, a rotation of the cutting member trigger 16, etc.

It will be appreciated that according to various embodiments, the movement arm 50, the coupling member 118, the cutting member trigger 16 and the cutting member 18 may be considered components of the coupling system of the electrosurgical instrument 10.

Jaw Lock System

When using an electrosurgical instrument 10 as described above, once the tissue positioned between the first and second jaws 30, 38 is grasped and compressed, it may be desirable to lock the first and second jaws 30, 38 at that position. This allows the operator to remove his or her fingers from the finger rings 26, 32 and use the electrosurgical instrument 10 in a manner similar to a surgical clamp. The electrosurgical instrument 10 should only lock when desired and not automatically.

For embodiments of the electrosurgical device 10 which include the jaw lock system, the second arm 22 includes the compression circuit 68 and the compression circuit button 66. The compression circuit 68 and the compression circuit button 66, together with the lock button 40, the switch arm 42, the biasing member 44 and the switch arm slot 48 may be considered components of the jaw lock system of the electrosurgical instrument 10. Additional details of the jaw locking system can be found, for example, in U.S. patent application Ser. Nos. 14/579,299, 14/579,599 and 14/579,623, the contents of which are hereby incorporated by reference in their entireties.

The lock button 40 is positioned between the cover member 46 and the first portion 34a of the housing 34, is accessible by a finger positioned in the finger ring 26, is pivotably connected to the first portion 34a of the housing 34 and is actuatable between a first position (e.g., a locked position) and a second position (e.g., an unlocked position). The switch arm 42 is pivotably connected to the first portion 34a of the housing 34, is movable between a first position and a second position and is in contact with the biasing member 44. With the lock button 40 in its first position, as the first and second jaws 30, 38 are moved toward the closed position and the bottom end of the switch arm 42 is about to be received by the top portion of the switch arm slot 48, the biasing member 44 is in a relaxed or minimally compressed state and is in contact with the switch arm 42, and a top end of the switch arm 42 is in contact with a proximal end of the lock button 40. This may be considered a neutral position of the switch arm 42. The top end of the switch arm 42 operates to prevent the lock button 40 from moving, effectively locking the lock button 40 in the first position.

As the first and second jaws 30, 38 are moved further toward the closed position, the bottom end of the switch arm 42 advances toward the bottom end of the switch arm slot 48, and the configuration of the switch arm slot 48 causes the bottom end of the switch arm 42 to move distally, thereby causing the top end of the switch arm 42 to move proximally and compress the biasing member 44. With the top end of the switch arm 42 moved proximally, pressure can be applied to the proximal end of the lock button 40 to move the lock button 40 past the top end of the switch arm 42 and into its second position where the lock button 40 is in contact with a portion (e.g., a notch) of the switch arm 42. When the lock button 40 is in this position, the switch arm 42 cannot be rotated by the force of the biasing spring 44, thus locking the switch arm 42 in position and allowing the first and second jaws 30, 38 to be locked in the closed position. In this position, the lower end of the switch arm 42 has compressed the compression circuit button 68 and the compression circuit 66 can signal the electrosurgical energy source 12 accordingly.

To move the lock button 40 back to its first position, pressure is applied to the distal end of the lock button 40 to cause the lock button 40 to move away from the portion/notch of the switch arm 42. With the lock button 40 no longer in contact with the portion/notch of the switch arm 42, the biasing member 44 drives the switch arm 42 back to its neutral position. As the switch arm 42 is being driven back to its neutral position, the lower end of the switch arm 42 releases the compression circuit button 68 and the compression circuit 66 may send a different signal to or stop signaling the electrosurgical energy source 12. Once the switch arm 42 is back in its neutral position, the switch arm 42 can exit the switch arm slot 48.

Electrosurgical Energy Activation System

For embodiments which include the sealing system, the electrosurgical energy that seals or coagulates tissue positioned between the first and second jaws 30, 38 should only be activated at the desired time. Specifically, it may be desirable to activate the electrosurgical energy only when the first and second jaws 30, 38 are applying sufficient pressure to tissue positioned therebetween. This typically occurs when the first and second arms 20, 22 are in the closed position and one of the first and second arms 20, 22 is possibly flexing to provide a load on the distal ends of the first and second jaws 30, 38. Thus it is desirable that the electrosurgical activation be disabled unless the first and second jaws 30, 38 are fully closed. It is also desirable, however, for the operator to be able to close the first and second jaws 30, 38 without activating the electrosurgical energy.

The delivery of electrosurgical energy to the electrode 60 may be activated in different ways. For example, according to various embodiments, the delivery of electrosurgical energy to the electrode 60 may be activated by moving the energy button 54 from its "open" position to its "closed" position. According to other embodiments, the delivery of electrosurgical energy to the electrode 60 may be activated by moving the compression circuit button 66 from its "open" position to its "closed" position. According to yet other embodiments, the delivery of electrosurgical energy to the electrode 60 may be activated by moving the energy button 54 from its "open" position to its "closed" position and moving the compression circuit button 66 from its "open" position to its "closed" position. In view of the above, it will be appreciated that the energy button 54, the energy button circuit 56, the compression circuit button 66 and the compression circuit 68, as well as the lock button 40, the switch arm 42 and the switch arm slot 48 may be considered components of the electrosurgical energy activation system of the electrosurgical instrument 10. Additional details of the electrosurgical energy activation system can be found, for example, in U.S. patent application Ser. Nos. 14/579,299, 14/579,599 and 14/579,623, the contents of which are hereby incorporated by reference in their entireties.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

What is claimed is:

1. An electrosurgical instrument, comprising:
a first arm comprising a first finger ring and a first jaw;
a second arm pivotally connected to the first arm, the second arm comprising:
a second finger ring;
a second jaw;
a cutting member movable within the first and second jaws; and
a cutting member trigger;
a coupling system comprising a coupling member mechanically coupled to the cutting member trigger, wherein the coupling member is movable between a first position and a second position, wherein:
in the first position of the coupling member, the coupling member is mechanically uncoupled from the cutting member; and
in the second position of the coupling member, the coupling member is in contact with the cutting member; and
a movement arm mechanically coupled to the first and second arms, wherein the movement arm is configured to move the coupling member toward contact with the cutting member as the first and second jaws are moved toward a closed position.

2. The electrosurgical instrument of claim 1, wherein:
a proximal end of the first arm is movable from a minimum distance from a proximal end of the second arm to a maximum distance from the proximal end of the second arm, wherein:
in the first position of the coupling member, the proximal end of the first arm is located at the maximum distance from the proximal end of the second arm; and
in the second position of the coupling member, the proximal end of the first arm is located at the minimum distance from the proximal end of the second arm.

3. The electrosurgical instrument of claim 1, wherein:
the movement arm is movable between a first position and a second position, wherein:
in the first position of the movement arm, the movement arm is spaced apart from the coupling member; and
in the second position of the movement arm, the movement arm is in contact with the coupling member.

4. The electrosurgical instrument of claim 3, wherein:
the second arm defines a slot;
the coupling system further comprises a pin which mechanically couples the movement arm to the second arm;
the pin is slidably movable within the slot; and
the movement arm is movable along the slot.

5. The electrosurgical instrument of claim 1, wherein the coupling member is pivotably connected to the cutting member trigger.

6. The electrosurgical instrument of claim 5, wherein:
the coupling system further comprises a biasing member in contact with the coupling member, wherein the biasing member is configured to bias the coupling member away from the cutting member, wherein:
in the first position of the coupling member, the biasing member is in an uncompressed state; and in the second position of the coupling member, the biasing member is in a compressed state.

7. The electrosurgical instrument of claim 1, wherein the cutting member defines a notch configured to receive the coupling member.

8. The electrosurgical instrument of claim 1, wherein:
the cutting member defines a receptacle;
the coupling member comprises a protuberance; and
the receptacle is configured to receive the protuberance, wherein engagement of the protuberance with the receptacle allows for the cutting member to be advanced distally.

9. The electrosurgical instrument of claim 1, further comprising:
a first protuberance connected to the cutting member; and
a second protuberance mechanically coupled to the cutting member trigger, wherein at least a portion of the first protuberance is axially aligned with at least a portion of the second protuberance, and wherein engagement of the second protuberance with the first protuberance allows for the cutting member to be retracted regardless of a position of the first jaw and a position of the second jaw.

10. The electrosurgical instrument of claim 1, wherein:
the second jaw comprises an electrode; and
the electrosurgical instrument is configured to selectively apply electrosurgical energy to the electrode.

11. The electrosurgical instrument of claim 1, wherein:
the first jaw defines a first channel;
the second jaw defines a second channel, wherein the first and second channels are axially aligned; and
the cutting member is movable within the first and second channels.

12. An electrosurgical instrument, comprising:
a first arm comprising a first finger ring and a first jaw;
a second arm pivotally connected to the first arm, the second arm comprising:
a second finger ring;
a second jaw comprising an electrode configured to apply electrosurgical energy to a tissue positioned between the first and second jaws;
a cutting member movable within the first and second jaws, wherein the cutting member is configured to cut the tissue positioned between the first and second jaws; and
a cutting member trigger;
a coupling system comprising a coupling member mechanically coupled to the cutting member trigger, wherein the coupling member is movable between a first position and a second position, wherein:
in the first position of the coupling member, the coupling member is mechanically uncoupled from the cutting member and movement of the cutting member trigger does not produce distal movement of the cutting member; and
in the second position of the coupling member, the coupling member is in contact with the cutting member and movement of the cutting member trigger produces distal movement of the cutting member; and
a movement arm mechanically coupled to the first and second arms, wherein the movement arm is configured to move the coupling member toward contact with the cutting member as the first and second jaws are moved toward a closed position.

13. The electrosurgical instrument of claim 12, wherein the first arm is movable from a first position to a second position, and wherein:
in the first position of the first arm, the first and second jaws are in an open position; and
in the second position of the first arm, the first and second jaws are in a closed position.

14. The electrosurgical instrument of claim 12, wherein the coupling system further comprises a biasing member in contact with the coupling member, wherein the biasing member is configured to bias the coupling member away from the cutting member.

15. The electrosurgical instrument of claim 12, wherein the movement of the cutting member trigger comprises at least one of the following:
a distal movement of the cutting member trigger;
a proximal movement of the cutting member trigger; and
a rotational movement of the cutting member trigger.

16. An electrosurgical instrument, comprising:
a first arm comprising a first finger ring and a first jaw;
a second arm pivotally connected to the first arm, the second arm comprising:
a second finger ring;
a second jaw comprising an electrode configured to apply electrosurgical energy to a tissue positioned between the first and second jaws;
a cutting member movable within the first and second jaws, wherein the cutting member is configured to cut the tissue positioned between the first and second jaws; and
a cutting member trigger;
a coupling system comprising a coupling member mechanically coupled to the cutting member trigger, wherein the coupling member is movable between a first position and a second position, wherein:
in the first position of the coupling member, the coupling member is mechanically uncoupled from the cutting member; and
in the second position of the coupling member, the coupling member is in contact with the cutting member; and
a movement arm mechanically coupled to the first and second arms, wherein the movement arm is configured to move the coupling member toward contact with the cutting member as the first and second jaws are moved toward a closed position.

17. The electrosurgical instrument of claim 16, wherein:
the first arm is movable between an open position and a closed position;
the coupling member is in the first position when the first arm is in the open position; and
the coupling member is in the second position when the first arm is in the closed position.

18. The electrosurgical instrument of claim 16, wherein:
the first jaw is movable between an open position and the closed position;
the coupling member is in the first position when the first jaw is in the open position; and
the coupling member is in the second position when the first jaw is in the closed position.

* * * * *